(12) United States Patent
Wang et al.

(10) Patent No.: US 9,192,696 B2
(45) Date of Patent: Nov. 24, 2015

(54) ARTIFACT FOR OSSEOUS REPAIR AND METHOD FOR FORMING THE SAME

(71) Applicant: Far Eastern New Century Corporation, Taipei (TW)

(72) Inventors: Jo-Ling Wang, Taipei (TW); Hui-Wan Chen, Taipei (TW)

(73) Assignee: FAR EASTERN NEW CENTURY CORPORATION, Taipei (TW)

( * ) Notice: Subject to any disclaimer, the term of this patent is extended or adjusted under 35 U.S.C. 154(b) by 130 days.

(21) Appl. No.: 14/026,964

(22) Filed: Sep. 13, 2013

(65) Prior Publication Data

US 2014/0128975 A1    May 8, 2014

(30) Foreign Application Priority Data

Nov. 5, 2012 (TW) .............................. 101140983 A

(51) Int. Cl.
| A61L 27/58 | (2006.01) |
| A61L 27/56 | (2006.01) |
| A61L 27/30 | (2006.01) |
| A61L 27/46 | (2006.01) |
| D01D 5/00 | (2006.01) |

(52) U.S. Cl.
CPC ............... *A61L 27/58* (2013.01); *A61L 27/306* (2013.01); *A61L 27/46* (2013.01); *A61L 27/56* (2013.01); *A61L 2430/02* (2013.01); *D01D 5/0007* (2013.01)

(58) Field of Classification Search
CPC ......... A61L 27/58; A61L 27/28; A61L 27/30; A61L 27/306; A61L 27/32; A61L 27/34
See application file for complete search history.

(56) References Cited

U.S. PATENT DOCUMENTS

| 7,547,449 | B2 | 6/2009 | Gower et al. | |
| 8,742,072 | B2 * | 6/2014 | Thorne | .......................... 530/356 |
| 2006/0247772 | A1 * | 11/2006 | McKay | ...................... 623/17.11 |

FOREIGN PATENT DOCUMENTS

EP          2458044          5/2012

OTHER PUBLICATIONS

Michele Iafisco et al., "Electrospun Nanostructured Fibers of Collagen-2 Biomimetic Apatite on Titanium Alloy," Hindawi Publishing Corp, Bioinorganic Chemistry and Application, vol. 2012, Article ID 123953 (8 pages).
Amir A. Al-Munajjed et al., "Development of a Biomimetic Collagen-Hydroxyapatite Scaffold for Bone Tissue 5 Engineering Using a SBF Immersion Technique," (29 pages), J Biomed Mat Res B: Appl Biomat; 2009, vol. 90, No. 2, pp. 534-591.
Sang-Hoon Rhee et al., "Nucleation of Hydroxyapatite Crystal through Chemical Interaction with Collagen," J. Am. Ceram. Soc. 83 [11] 2890-92 (2000) (3 pages).

* cited by examiner

*Primary Examiner* — Allison Fox
(74) *Attorney, Agent, or Firm* — DLA Piper LLP (US)

(57) ABSTRACT

An artifact for osseous repair includes a bioresorbable porous cage defining an internal space, and a biocompatible composite which includes a plurality of mineralized collagen-mimic fibrils filled in the internal space of the bioresorbable porous cage.

15 Claims, No Drawings

US 9,192,696 B2

ARTIFACT FOR OSSEOUS REPAIR AND METHOD FOR FORMING THE SAME

CROSS-REFERENCE TO RELATED APPLICATION

This application claims priority of Taiwanese application no. 101140933, filed on Nov. 5, 2012.

BACKGROUND OF THE INVENTION

1. Field of the Invention

This invention relates to an artifact for osseous repair and a method for forming the same.

2. Description of the Related Art

U.S. Pat. No. 7,537,449 discloses a process for making a composite involving the inclusion of acidic polymers to a supersaturated mineralizing solution, in order to induce an amorphous liquid-phase precursor to an inorganic mineral, which is then absorbed (pulled by capillary action) into an organic matrix. By such process, the inorganic mineral crystals can be embedded within collagen fibers of the organic matrix.

European patent application publication no. 2458044 discloses a product for enhancing tissue growth and/or tissue adhesion. The product includes a carrier material that is built up from electrospun nanofibers. Polarised or charged nanocrystals are chemically and/or physically bonded to the carrier material.

Methods for producing mineralized collagen fibers are, for example, disclosed in: (1) Michele Iafisco et al., "Electrospun Nanostructured Fibers of Collagen-Biomimetic Apatite on Titanium Alloy," Hindawi Publishing Corp, Bioinorganic Chemistry and Application, vol. 2012, Article ID 123953, 8 pages; (2) Amir A. Al-Munajjed et al., "Development of a Biomimetic Collagen-Hydroxyapatite Scaffold for Bone Tissue Engineering using a SBF Immersion Technique," Published online 29 Jan. 2009 in Wiley InterScience; and (3) Sang-Hoon Rhee et al., "Nucleation of Hydroxyapatite Crystal through Chemical Interaction with Collagen," J. Am, Ceram, Soc. 83 [11] 2890-92 (2000).

SUMMARY OF THE INVENTION

An object of the present invention is to provide an artifact for osseous repair which is suitable for growth of bone cells thereon and adhesion of the bone cells thereto. Another object of the present invention is to provide a method for forming the artifact for osseous repair. With the method of the present invention, the artifact can be formed in a simplified way.

According to a first aspect of the present invention, an artifact for osseous repair includes a bioresorbable porous cage defining an internal space, and a biocompatible composite which includes a plurality of mineralized collagen-mimic fibrils filled in the internal space of the bioresorbable porous cage. With the protection of the bioresorbable porous cage, the biocompatible composite is less likely to breakdown upon exposure to body fluids.

According to a second aspect of the present invention, a method for forming an artifact for osseous repair includes the steps of:

(a) electrospinning a fibrillar organic matrix to obtain collagen-mimic floss that includes a plurality of collagen-mimic fibrils;

(b) dispersing the collagen-mimic fibrils in a liquid solution of a calcium ion-containing precursor to obtain a collagen-mimic fibrils-containing dispersion; and (c) gradually adding a liquid solution of a phosphate ion-containing precursor into the collagen-mimic fibrils-containing dispersion such that the calcium ion-containing precursor is permitted to react with the phosphate ion-containing precursor in vicinity of the collagen-mimic fibrils so as to form a mineral component deposited on the collagen-mimic fibrils, thereby obtaining the mineralized collagen-mimic fibrils.

DETAILED DESCRIPTION OF THE PREFERRED EMBODIMENTS

A preferred embodiment of an artifact for osseous repair includes a biocompatible composite and a bioresorbable porous cage that is configured to embrace therein the biocompatible composite.

The bioresorbable porous cage functions to reinforce the biocompatible composite, and is suitable for growth of bone cells thereon and adhesion of the bone cells thereto. The bioresorbable porous cage prevents the breakdown of the biocompatible composite when the latter is exposed to body fluids. The bioresorbable porous cage allows the bone cells to grow inwardly through pores thereof, thereby enabling the artifact to serve as a temporary bone substitute.

The bioresorbable porous cage is made by molding a fixture including a vaporizable material and a bioresorbable material, followed by vaporizing the vaporizable material through heating. The bioresorbable material includes water and calcium sulfate. The vaporizable material is selected from camphor, menthol and naphthalene.

The calcium sulfate may be in anhydrous, hemihydrate ($CaSO_4 \cdot 0.5H_2O$), or dihydrate ($CaSO_4 2H_2$)) form. The water has an amount ranging from 18 wt % to 23.1 wt % based on the total weight of the bioresorbable material. If the amount of the water is lower than 18 wt %, the calcium sulfate cannot be evenly mixed with water. If the amount of the water is higher than 23.1 wt %, the resultant bioresorbable porous cage may have a reduced compression strength.

A mineral material may be added to the mixture for molding the bioresorbable porous cage if the addition thereof will not adversely affect the functions of the bioresorbable porous cage. Examples of the mineral material are substantially the same as those of a mineral component of the biocompatible composite (as will be described later).

The bioresorbable porous cage has an internal space-defining wall which defines an internal space for receiving the biocompatible composite, and which has a thickness ranging from 11.5% to 17.5% of a maximum dimension of the bioresorbable porous cage in cross section. The bioresorbable porous cage has a plurality of pores that are fluidly communicated with the internal space and that have an average pore sire ranging from 150 μm to 500 μm. In order to provide the bioresorbable porous cage with a compression strength greater than 16 MPa, the bioresorbable porous cage preferably has the pores with an average pore size ranging from 150 μm to 300 μm, and a porosity ranging from 5 vol. % to 50 vol % based on the total volume of the bioresorbable porous cage. In other preferred embodiments, the bioresorbable porous cage may have the pores with an average pore size ranging from 300 μm to 500 μm, and a porosity ranging from 5 vol % to 30 vol % based on the total volume of the bioresorbable porous cage, and may still have a compression strength greater than 16 MPa.

The biocompatible composite includes a plurality of mineralized collagen-mimic fibrils made by the following steps (a) to (d).

In step (a), a fibrillar organic matrix is electrospun to obtain collagen-mimic floss that includes a plurality of collagen-mimic fibrils. Examples of the fibrillar organic matrix include, but are not limited to, polysaccharide, polysaccharide derivatives, polypeptide, polypeptide derivatives, polylactic acid; polyglycolic acid, polyethylene oxide, polyethylene glycol, polycaprolactone, polyvinyl alcohol, polyacrylic acid, polyglycolic acid, and copolymers thereof. Examples or the polysaccharide include, but are not limited to, chitin, cellulose, alginic acid, and combinations thereof. The polysaccharide derivatives may be salts of polysaccharide. Examples of the polypeptide derivatives include, but are not limited to, gelatin, collagen, collagen derivatives, and combinations thereof.

Preferably; the collagen-mimic fibrils have an average length ranging from 3.5 mm to 7 mm. When the average length of the collagen-mimic fibrils is not within the above range, the mineralized collagen-mimic fibrils are less likely to entangle with one another in the subsequent steps, which may adversely affect a flexural strength of the biocompatible composite. In addition, the entangled and mineralized collagen-mimic fibrils provide a plurality of hole zones which are suitable for growth and adhesion of the bone cells.

In step (b), the collagen-mimic fibrils are dispersed in a liquid solution of a calcium ion-containing precursor to obtain a collagen-mimic fibrils-containing dispersion. Examples of calcium ion-containing precursor include, but are not limited to, calcium chloride, calcium carbonate, calcium nitrate, calcium hydroxide, calcium acetate, calcium gluconate, calcium citrate, and combinations thereof.

In step (c), a liquid solution of a phosphate ion-containing precursor is gradually added into the collagen-mimic fibrils-containing dispersion such that the calcium ion-containing precursor is permitted to react with the phosphate ion-containing precursor in vicinity of the collagen-mimic fibrils so as to form a mineral component deposited on the collagen-mimic fibrils, thereby obtaining the mineralized collagen-mimic fibrils. Preferably, in this step, while the liquid solution of the phosphate ion-containing precursor is added dropwise info the collagen-mimic fibrils-containing dispersion, the collagen-mimic fibrils-containing dispersion is stirred such that the collagen-mimic fibrils in the dispersion are evenly dispersed.

In step (d), the collagen-mimic fibrils-containing dispersion is further stirred at a speed higher than that in step (c) so as to facilitate entanglement of the mineralized collagen-mimic fibrils with one another.

In this embodiment, the calcium ion-containing precursor reacts with the phosphate ion-containing precursor to obtain a calcium phosphate (i.e., the mineral component). Examples of the phosphate ion-containing precursor include, but are not limited to, tertiary potassium phosphate, mono sodium phosphate, disodium phosphate, trisodium phosphate, diammonium hydrogen phosphate, monoammonium phosphate, triammonium phosphate, tetrasodium pyrophosphate, monopotassium phosphate, dipotassium hydrogen phosphate, and combinations thereof. Examples of the calcium phosphate include, but are not limited to, $Ca(HPO_4).H_2O$, $Ca(HPO_4)_2.H_2O$, $CaHPO_4$, $Ca(H_2PO_4)_2.H_2O$, $Ca_{10}(PO_4)_6(OH)_2$, $Ca_{10}(PO_4)_6(F)_2$, $Ca_8(HPO_4)_2(PO_4)_4.5H_2O$, $Ca_4(PO_4)_2O$, $Ca_2(PO_4)_2$, $Na_2O$—$CaO$—$SiO_2$—$P_2O_5$, and combinations thereof. In other preferred embodiments, the mineral component is bioglass mainly composed of $SiO_2$, $Na_2O$, $CaO$ and $P_2O_5$ ($Na_2O$—$CaO$—$SiO_2$—$P_2O_5$). It should be noted that the presence of the mineral component on the surface of the collagen-mimic fibrils retards the degradation of collagen-mimic fibrils and reinforces the strength of the collagen-mimic fibrils.

The artifact of this invention may further include an amount of a bone growth factor to stimulate bone growth, if the functions of the artifact of this invention will not be adversely affected. Examples of the bone growth factor include, but are not limited to, an osteoinductive growth factor, a platelet-derived growth factor, a transforming growth factor, an insulin-like growth factor, etc. Examples of the osteoinductive growth factor include, but are not limited to, bone morphogenetic protein, ostercalcin, osteogenin, etc.

The present invention will now be explained in more detail below by way of the following examples.

Preparation of Collagen-Mimic Floss

Example F1

0.3 g of collagen (Sigma Aldrich, Bornstein and Traub Type I collagen (Sigma Type III)) was dissolved in 5 ml of 1,1,1,3,3,3 hexafluoro-2-propanol (Fluka, 99%) to obtain a collagen solution (6 wt %). The collagen solution was subjected to electrospinning at 20 kV using an electrospinning device (Taiwan Textile Research Institute, COSMISC-PME30). The collagen solution was accelerated to flow out from a nozzle tip of the electrospinning device toward a collector at a flow rate of 0.8 ml/hr to obtain collagen floss that includes a plurality of collagen fibrils. A distance from the nozzle tip to the collector was set to be 7 cm. The collagen floss was cleaned first with a methanol aqueous solution (30 wt %), and then with another methanol aqueous solution (60 wt %), and was subsequently freeze-dried. The collagen fibrils had an average length of 0.7 mm.

Example F2

Collagen floss was prepared following the procedure employed in Example F1 except that the flow rate was 0.45 ml/hr. The average length of the collagen fibrils of the collagen floss obtained in this example was 3.5 ram.

Example F3

0.35 g of chitin (Sigma Aldrich) was dissolved in 5 ml of trifluoroacetic acid (Sigma Aldrich, 99%, ReagentPlus®) to obtain a chitin solution (7 wt %). The chitin solution was subjected to electrospinning at 20 kV using an electrospinning device (Taiwan Textile Research Institute, COSMISC-PME30). The chitin solution was accelerated to flow out from a nozzle tip of the electrospinning device toward a collector at a flow rate of 0.8 ml/hr to obtain chitin floss that includes a plurality of chitin fibrils. A distance from the nozzle tip to the collector was set to be 5 cm. The chitin floss was cleaned first with a methanol, aqueous solution (30 wt %), and then with another methanol aqueous solution (60 wt %), and was subsequent freeze-dried. The chitin fibrils had an average length of 4.5 mm.

Example F4

Collagen floss was prepared following the procedure employed in Example F1 except that the flow rate was 0.3 ml/hr. The average length of the collagen fibrils of the collagen floss obtained in this example was 6.8 mm.

Example F5

Collagen floss was prepared following the procedure employed in Example F1 except that the flow rate was 0.15 ml/hr. The average length of the collagen fibrils of the collagen floss obtained in this example was 13 mm.

[Preparation of Bioresorbable Sample]

Example S1

A mixture including wafer (18.03 wt %) and calcium sulfate hemihydrates (81.97 wt %, Sigma Aldrich) was molded in a stainless steel cylinder mold at 80° C. for 24 hours. The stainless steel cylinder mold had a height of 12 mm, and an outer surrounding wall with a diameter of 6 mm. The mixed material was molded to obtain a bioresorbable cylinder having a height of 12 mm and a diameter of 6 mm.

Example S2

A bioresorbable sample was prepared following the procedure employed in Example S1 except that the mixture included 23.08 wt % of water and 76.92 wt % of calcium sulfate hemihydrates, and that the mixture material was molded at room temperature. The obtained bioresorbable sample had a thickness of 2 mm.

Example S3

A bioresorbable sample was prepared following the procedure employed in Example S2 except that the mixture included 33.33 wt % of water and 66.67 wt % of calcium sulfate hemihydrates. The obtained bioresorbable sample had a thickness of 2 mm.

Preparation of Bioresorbable Porous Cage

Example C1

A bioresorbable material including water (18.03 wt %) and calcium sulfate hemihydrates (81.97 wt %, Sigma Aldrich) was mined with camphor, and the mixture material was molded in a stainless steel cylinder mold at 80° C. for 24 hours. The stainless steel cylinder mold had a height of 12 mm, an inner surrounding wall with an outer diameter of 4 mm, and an outer surrounding wall with an inner diameter of 6 mm. The mined material was molded between the inner and outer surrounding walls to obtain a bioresorbable porous cage which had a pore sire of about 300~400 μm, a porosity of about 20~25 vol %, and a thickness of 2 mm.

Preparation of Mineralized Collagen-Mimic Fibrils (Biocompatible Composite)

Example M1

1 g of collagen floss of Example F1 was evenly dispersed in 14 ml of a calcium chloride aqueous solution (0.1M, calcium chloride was available from Sigma Aldrich; to obtain a collagen fibrils-containing dispersion. The collagen fibrils-containing dispersion was stirred at about 120 rpm using a magnetic stirrer so as to evenly disperse the collagen fibrils, while 8.4 ml of a disodium phosphate aqueous solution (0.1M) was slowly added thereto at a rate of 0.5 ml/min. During addition of the disodium phosphate aqueous solution to the collagen fibrils-containing dispersion, the calcium ion was precipitated as calcium phosphate distributed evenly on the surfaces of the collagen fibrils, thereby obtaining mineralized collagen fibrils in the dispersion. Then the pH of the collagen fibrils-containing dispersion was adjusted to 7.0 using a sodium hydroxide aqueous solution (0.1M), and the dispersion, was stirred for one hour at a rate of 350 rpm to facilitate entanglement of the mineralized collagen fibrils with one another, and was filtrated to obtain a filter cake. Subsequently, the filter cake was subjected to a purifying step by cleaning the filter cake using twice distilled water, followed by centrifugation to obtain a precipitate. The precipitate was subjected to the aforesaid purifying step three times, and freeze-dried to obtain the mineralized collagen fibrils (a biocompatible composite).

Example M2

A biocompatible composite including mineralized collagen fibrils was prepared following the procedure employed in Example M1 except that the collagen floss of Example F2 was used instead of the collagen floss of Example F1.

Example M3

A biocompatible composite including mineralized chitin fibrils was prepared following the procedure employed in Example M1 accept that the chitin floss of Example F3 was used instead of the collagen floss of Example F1. The biocompatible composite was further pressed into a plate form to have a thickness of 4 mm, and cut into a square of 2 cm×2 cm.

Example M4

A biocompatible composite including mineralized collagen fibrils was prepared following the procedure employed in Example M1 except that the collagen, floss of Example F4 was used instead of the collagen floss of Example F1. The biocompatible composite was further pressed into a plate form to have a thickness of 4 mm, and cut into a square of 2 cm×2 cm.

Example M5

A biocompatible composite including mineralized collagen fibrils was prepared following the procedure employed in Example M1 except that the collagen floss of Example F5 was used instead of the collagen floss of Example F1.

Preparation of Artifact for Osseous Repair

Example A1

The mineralized collagen fibrils of Example M1 were disposed in an infernal space of the bioresorbable porous cage of Example C1, which were then subjected to freeze-drying, thereby obtaining an artifact of this invention.

Example A2

An artifact was prepared by disposing the collagen floss of Example F1 in an internal space of the bioresorbable porous cage of Example C1, followed by freeze-drying.

Example A3

An artifact was prepared by molding the mineralized collagen fibrils of Example M1 using the stainless steel cylinder mold mentioned in Example C1, followed by freeze-drying.

Comparative Example A4

An artifact was prepared by molding the collagen floss of Example F1 using the stainless steel cylinder mold mentioned in Example C1, followed by freeze-drying.

Comparative Example A5

Hydroxyapatite and calcium sulfate were mixed at a weight ratio of 1:1 to obtain a mixture. 7.5 g of the mixture was then mixed with 2.5 ml of water to obtain a slurry for osseous repair.

Comparative Example A6

Hydroxyapatite and calcium sulfate were mixed at a weight ratio of 1:1 to obtain a mixture. 7.5 g of the mixture was then mixed with 2.5 ml of a collagen solution (2 wt %) to obtain a slurry for osseous repair.

Compression Strength Test

The bioresorbable samples of S1 to S3 were subjected to a compression strength test performed in accordance with ISO 5833. The results are shown in Table 1.

TABLE 1

| Example | Water content (wt %) | Compression strength (MPa) |
|---|---|---|
| S1 | 18.03 | 45.6 |
| S2 | 23.08 | 38.7 |
| S3 | 33.33 | 22.4 |

From the results shown in Table 1, it was found that when the water content was in the range of 18.03 wt % to 23.08 wt %, the bioresorbable sample had relatively good compression strength (38.7 MPa~45.6 MPa).

The mixture for forming the bioresorbable sample S1 was mixed with camphor in different ratios to obtain a plurality of bioresorbable porous cases with different porosities. Those cages were subjected to a compression strength test performed in accordance with ISO 5833. The results are shown in Table 2.

TABLE 2

| Porosity | Pore size (S, μm) | | |
|---|---|---|---|
| (P, vol %) | 150 < S < 300 | 300 < S < 400 | 400 < S < 500 |
| 0 | 27.6 | 26.8 | 27.1 |
| 0 < P < 10 | 26.1 | 24.5 | 23.6 |
| 10 < P < 20 | 24.2 | 20.1 | 19.4 |
| 20 < P < 30 | 21.9 | 17.8 | 16.4 |
| 30 < P < 40 | 17.4 | 12.3 | 11.2 |
| 40 < P < 50 | 16.1 | 10.8 | 9.4 |
| 50 < P < 60 | 14.7 | — | — |
| 60 < P < 70 | 11.2 | — | — |

From the results shown in Table 2, it was found that in order to provide the bioresorbable porous cage with a compression strength greater than 16 MPa, the bioresorbable porous cage preferably had the pores with an average pore size ranging from 150 μm to 300 μm, and a porosity ranging frost 5 vol % to 50 vol % based on the total volume of the bioresorbable porous cage. In addition, the bioresorbable porous cage might hare the pores with an average pore size ranging from 300 μm to 500 μm, and a porosity ranging from 5 volt to 30 vol. % based on the total volume of the bioresorbable porous cage. Although the bioresorbable porous cage had a good compression strength when it had the porosity of zero, the same would not facilitate the bone cells to grow inwardly through the pores, and was anticipated to have a poor cell viability.

The artifacts of Examples A1 to A3 and Comparative Example A4 were subjected to a compression strength test performed in accordance with ISO 5833. The results are shown in Table 3.

TABLE 3

| Artifact | Compression strength (MPa) |
|---|---|
| Example A1 | 26.9 |
| Example A2 | 14.4 |
| Example A3 | 9.1 |
| Comparative Example A4 | 3.2 |

From the results of Table 3, it was found that the artifact of Example A1 in which the mineralized collagen fibrils were protected by a bioresorbable porous cage had a better compression strength than that of Example A3 in which the mineralized collagen fibrils were not protected by a bioresorbable porous cage. The artifact of Example A3 had a better compression strength than, that of Comparative Example A4 in which the collagen fibrils were not mineralized.

Flexural Strength Test

The biocompatible composites of Examples M1 to M5 were subjected to a flexural strength test performed in accordance with ISO 178. The results are shown in Table 4.

TABLE 4

| Biocompatible composite | Fibril | Fibril length (mm) | Flexural strength (MPa) |
|---|---|---|---|
| Example M1 | Mineralized collagen fibrils | 0.7 | 0.84 |
| Example M2 | Mineralised collagen fibrils | 3.5 | 1.73 |
| Example M3 | Mineralized chitin fibrils | 4.5 | 1.79 |
| Example M4 | Mineralized collagen fibrils | 6.8 | 2.06 |
| Example M5 | Mineralized collagen fibrils | 13 | 1.25 |

From the results shown in Table 4, it was found that when the average length of the collagen (chitin) fibrils ranged from 3.5 to 6.8, the mineralized collagen, (chitin) fibrils had a flexural strength not less than 1.70 MPa.

Resistance to Effects of Simulated Body Fluid

Each of the artifacts of Examples A1 and A3 was disposed in a test tube of 15 ml, and 5 ml of a simulated body fluid (a phosphate buffered saline solution) was poured into the test tube. The test tube was then placed in a shaker bath at 100 rpm, and agitated at 37° C. for 24 hours. Thereafter, the simulated body fluid in each test tube was observed. It was observed that the simulated body fluid for testing the artifact of Example A1 was still clear, whereas that for testing the artifact of Example A3 was turbid. This means that without the protection of the bioresorbable porous cage, the mineralized collagen fibrils were likely to breakdown upon exposure to body fluids.

Cell Viability Detection and Ostercalcin Detection

A solution including water and calcium sulfate hemihydrates at a weight ratio of 0.22 was prepared. The biocompatible composites of Example M3 and M4, the artifacts of Examples A1 to A3, and the artifact of Comparative Example A4 were dispensed into a 96 well plate to serve as test samples M3, M4, and A1 to A4, to each of which 15 μl of the solution was added to allow the test samples M3, M4, and A1 to A4 to solidify. Thereafter, the test samples M3, M4, and A1 to A4 were irradiated by UV light for sterilization.

The artifacts of Comparative Examples A5 and A6 were also dispensed into the 96 well plate to serve as test samples A5 and A6. The test samples A5 and A6 were allowed to stand so as to became solidified, and were subsequently irradiated by UV light for sterilization.

$1 \times 10^4$ human osteoblast-like cells were added to each of the test samples M3, M4, and A1 to A6, and were cultured in each of the test samples at 37° C. for 7 days.

Thereafter, absorbance for each of the test samples at 570 nm was read on an ELISA reader scanning multi-well spectrophotometer (Biotek, powerwave XS) for cell viability detection. The higher the absorbance was, the more the cells could be found in the test sample. The results are shown in Tables 5 and 6.

In addition, absorbance for each of the test samples at 450 nm was read on the ELISA reader scanning multi-well spectrophotometer for ostercalcin detection using an ostercalcin immunoassay kit. The absorbance of each of the test samples was then converted to an ostercalcin concentration. The results are also shown in Tables 5 and 6.

TABLE 5

| Test samples | Structure | Cell viability (absorbance) | Ostercalcin concentration (ng/ml) |
|---|---|---|---|
| Example M3 | Mineralized chitin fribils | 0.862 | 39 |
| Example M4 | Mineralized collagen fibrils | 0.904 | 43 |
| Comparative Example A5 | Slurry including HAP and CaSO$_4$ | 0.388 | 16 |
| Comparative Example A6 | Slurry including HAP, CaSO$_4$ and collagen | 0.541 | 23 |

* HAP: Hydroxyapatite

From the results shown in Table 5, it was found that in comparison, with the slurry of Comparative Examples A5 or A6, the mineralized collagen (chitin) fibrils of Example M3 or M4 had a large number of viable cells.

TABLE 6

| Test samples | Structure | Cell viability (absorbance) | Ostercalcin concentration (ng/ml) |
|---|---|---|---|
| Example A1 | Mineralized collagen fibrils + porous cage | 0.924 | 45 |
| Example A2 | Non-mineralized collagen fibrils + porous cage | 0.918 | 36 |
| Example A3 | Molded mineralized collagen fibrils | 0.902 | 30 |
| Comparative Example A4 | Molded non-mineralized collagen fibrils | 0.881 | 24 |

From the results shown in Table 6, it was found that in comparison with the molded mineralized collagen fibrils of Example A3, the artifact of Example A1 had a larger number of viable cells. In addition, the molded mineralized collagen fibrils of Example A3 had a larger number of viable cells than the molded non-mineralized collagen fibrils of Comparative Example A4.

While the present invention has been described in connection with what are considered, the most practical and preferred embodiments, it is understood that this invention is not limited to the disclosed embodiments but is intended to cover various arrangements included within the spirit and scope of the broadest interpretations and equivalent arrangements.

What is claimed is:

1. An artifact for osseous repair, comprising:
   a bioresorbable porous cage defining an internal space; and
   a biocompatible composite which includes a plurality of mineralized collagen-mimic fibrils filled in the internal space of said bioresorbable porous cage.

2. The artifact of claim 1, wherein said bioresorbable porous cage has a porosity ranging from 5 vol % to 50 vol % based on the total volume of said bioresorbable porous cage.

3. The artifact of claim 2, wherein said bioresorbable porous cage has a plurality of pores which have an average pore size ranging from 150 µm to 500 µm.

4. The artifact of claim 1, wherein said bioresorbable porous cage has an internal space-defining wall which defines the internal space, and which has a thickness ranging from 11.5% to 17.5% of a maximum dimension of the bioresorbable porous cage in cross section.

5. The artifact of claim 1, wherein said bioresorbable porous cage is made from a bioresorbable material including calcium sulfate.

6. The artifact of claim 5, wherein said bioresorbable material further includes water in an amount ranging from 18 wt % to 23.1 wt % based on the total weight of said bioresorbable material.

7. The artifact of claim 1, wherein said mineralized collagen-mimic fibrils are made by the steps of:
   (a) electrospinning a fibrillar organic matrix to obtain collagen-mimic floss that includes a plurality of collagen-mimic fibrils;
   (b) dispersing said collagen-mimic fibrils in a liquid solution of a calcium ion-containing precursor to obtain a collagen-mimic fibrils-containing dispersion; and
   (c) gradually adding a liquid solution of a phosphate ion-containing precursor into said collagen-mimic fibrils-containing dispersion such that said calcium ion-containing precursor is permitted to react with said phosphate ion-containing precursor in vicinity of said collagen-mimic fibrils so as to form a mineral component deposited on said collagen-mimic fibrils, thereby obtaining said mineralized collagen-mimic fibrils.

8. The artifact of claim 7, wherein step (c) is implemented by stirring said collagen-mimic fibrils-containing dispersion while adding dropwise said liquid solution of said phosphate ion-containing precursor into said collagen-mimic fibrils-containing dispersion.

9. The artifact of claim 8, further comprising a step (d) of stifling said collagen-mimic fibrils-containing dispersion so as to facilitate entanglement of the mineralized collagen-mimic fibrils with one another.

10. The artifact of claim 7, wherein said fibrillary organic matrix is made from a material selected from the group consisting of polysaccharide, polysaccharide derivatives, polypeptide, polypeptide derivatives, polylactic acid, polyglycolic acid, polyethylene oxide, polyethylene glycol, polycaprolactone, polyvinyl alcohol, polyacrylic acid, polyglycolic acid, and copolymers thereof.

11. The artifact of claim 10, wherein said polysaccharide is selected from the group consisting of chitin, cellulose, alginic acid, and combinations thereof.

12. The artifact of claim 10, wherein said polypeptide derivatives are selected from the group consisting of gelatin, collagen, collagen derivatives and combinations thereof.

13. The artifact of claim 7, wherein said calcium ion-containing precursor is selected from calcium chloride, calcium carbonate, calcium hydroxide, calcium gluconate, calcium citrate, and combinations thereof.

14. The artifact of claim 7, wherein said mineral component includes a material selected from the group consisting of: $Ca(HPO_4).H_2O$, $Ca(HPO_4)_2.H_2O$, $CaHPO_4$, $Ca(H_2PO_4)_2.H_2O$, $Ca_{10}(PO_4)_6(OH)_2$, $Ca_{10}(PO_4)_6(F)_2$, $Ca_8(HPO_4)_2(PO_4)_4.5H_2O$, $Ca_4(PO_4)_2O$, $Ca_3(PO_4)_2$, $Na_2O\text{-}CaO\text{-}SiO_2\text{-}P_2O_5$, and combinations thereof.

15. The artifact of claim 7, wherein said collagen-mimic fibrils have an average length ranging from 3.5 mm to 7 mm.

* * * * *